US012102728B2

(12) United States Patent
Ko et al.

(10) Patent No.: US 12,102,728 B2
(45) Date of Patent: Oct. 1, 2024

(54) ELECTRONIC DEVICE WITH ANTIBACTERIAL EFFECT DETECTION AND PORTABLE DEVICE

(71) Applicant: Acer Incorporated, New Taipei (TW)

(72) Inventors: Chueh-Pin Ko, New Taipei (TW); Chih-Chiang Chen, New Taipei (TW)

(73) Assignee: ACER INCORPORATED, New Taipei (TW)

( * ) Notice: Subject to any disclaimer, the term of this patent is extended or adjusted under 35 U.S.C. 154(b) by 660 days.

(21) Appl. No.: 17/464,089

(22) Filed: Sep. 1, 2021

(65) Prior Publication Data
US 2022/0096694 A1 Mar. 31, 2022

(30) Foreign Application Priority Data
Sep. 30, 2020 (TW) ................................. 109134212

(51) Int. Cl.
| | |
|---|---|
| *A61L 2/28* | (2006.01) |
| *B08B 7/00* | (2006.01) |
| *H05K 5/02* | (2006.01) |
| *H05K 9/00* | (2006.01) |

(52) U.S. Cl.
CPC .............. *A61L 2/28* (2013.01); *B08B 7/0035* (2013.01); *H05K 5/0217* (2013.01); *H05K 9/0007* (2013.01); *A61L 2202/14* (2013.01); *B32B 2307/754* (2013.01)

(58) Field of Classification Search
CPC ........ A61L 2/28; A61L 2/232; A61L 2202/14; A61L 2202/16
See application file for complete search history.

(56) References Cited

U.S. PATENT DOCUMENTS
2021/0388217 A1* 12/2021 Gurvich ................. A01N 61/00

FOREIGN PATENT DOCUMENTS
| CN | 107734891 A | 2/2018 |
| CN | 110139518 A | 8/2019 |
| WO | WO 2019/164075 A1 | 8/2019 |

\* cited by examiner

*Primary Examiner* — Lessanework Seifu
(74) *Attorney, Agent, or Firm* — Birch, Stewart, Kolasch & Birch, LLP (57) ABSTRACT

An electronic device with antibacterial effect detection and a portable device are provided. The electronic device includes an antibacterial housing, a light emitting unit, a light receiving unit and a processing unit. The antibacterial housing has a concave hole, which gradually shrinks from the inside to the outside. The light emitting unit is arranged under the concave hole of the antibacterial housing. The light emitting unit is used for emitting a detection light toward an inclined side wall of the concave hole. The light receiving unit is arranged under the concave hole of the antibacterial housing. The light receiving unit is used for receiving a detection light reflected from the inclined side wall of the concave hole. The processing unit is used for analyzing the antibacterial effect of the antibacterial housing according to the detection light.

20 Claims, 8 Drawing Sheets

ELECTRONIC DEVICE WITH ANTIBACTERIAL EFFECT DETECTION AND PORTABLE DEVICE

This application claims the benefit of Taiwan application Serial No. 109134212, filed Sep. 30, 2020, the subject matter of which is incorporated herein by reference.

BACKGROUND OF THE INVENTION

Field of the Invention

The invention relates in general to an electronic device and a portable device, and more particularly to an electronic device with antibacterial effect detection and a portable device.

Description of the Related Art

Viruses and bacteria are everywhere in people's daily life. Some viruses are highly infectious and cannot be effectively prevented and may cause global pandemic. Research shows that human's hands are a main transmission route. When people touch elevator buttons, handles, mobile phones and laptops with their hands, viruses or bacteria may be adhered to their hands and further be transmitted to their mouths, faces or other parts of their body and make the carriers infected.

Research personnel are now developing an antibacterial function for electronic devices. Hopefully, electronic devices such as mobile phones and laptops that are commonly used in people's daily life can be provided with an antibacterial function and will not become a transmission route.

Moreover, the electronic devices commonly used in people's daily life must also be provided with antibacterial effect detection to assure the antibacterial effect.

SUMMARY OF THE INVENTION

The invention is directed to an electronic device with antibacterial effect detection and a portable device. A concave hole which gradually shrinks from the inside to the outside is arranged on the antibacterial housing, such that the detection light varies with the thickness of the antibacterial housing and the antibacterial effect of the antibacterial housing can be analyzed according to the detection light.

According to one embodiment of the present invention, an electronic device with antibacterial effect detection is provided. The electronic device includes an antibacterial housing, a light emitting unit, a light receiving unit and a processing unit. The antibacterial housing has a concave hole, which gradually shrinks from an inside of the antibacterial housing to an outside of the antibacterial housing. The light emitting unit is arranged under the concave hole of the antibacterial housing. The light emitting unit is used for emitting a detection light toward an inclined side wall of the concave hole. The light receiving unit is arranged under the concave hole of the antibacterial housing. The light receiving unit is used for receiving a detection light reflected from the inclined side wall of the concave hole. The processing unit is used for analyzing the antibacterial effect of the antibacterial housing according to the detection light.

According to another embodiment of the present invention, an electronic device with antibacterial effect detection is provided. The electronic device includes an antibacterial housing and a light emitting unit. The antibacterial housing has a concave hole, which gradually shrinks from an inside of the antibacterial housing to an outside of the antibacterial housing. The light emitting unit is arranged under the concave hole of the antibacterial housing. The light emitting unit is used for emitting a detection light toward the concave hole. A portable device receives the detection light reflected from the concave hole and analyzes an antibacterial effect of the antibacterial housing according to the detection light.

According to an alternate embodiment of the present invention, a portable device is provided. The portable device includes a light receiving unit and a processing unit. The light receiving unit is used for receiving a detection light reflected from a concave hole of an antibacterial housing of an electronic device. The concave hole gradually shrinks from an inside of the antibacterial housing to an outside of the antibacterial housing. The processing unit is used for analyzing an antibacterial effect of the antibacterial housing according to the detection light.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1:
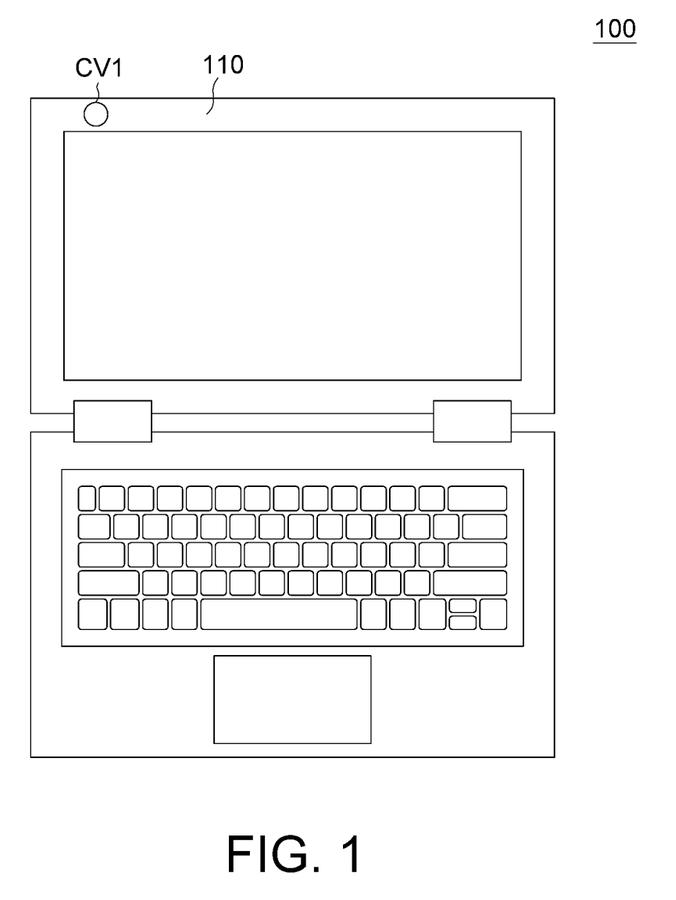
FIG. 1 is a schematic diagram of an electronic device according to an embodiment.

Referring to FIG. 1, a schematic diagram of an electronic device 100 according to an embodiment is shown. The electronic device 100 may be a laptop, a tablet, a keyboard, a mouse, a screen, a lamp or a mobile phone. The antibacterial housing 110 of the electronic device 100 may be a glass panel or plastic housing doped with silver ions or copper ions. When silver ions and copper ions which carry positive electricity touch microbial cells which carry negative electricity, silver ions and copper ions will be attached on the microbial cells. Silver ions and copper ions will pierce cell membrane, damage DNA and inhibit protein formation, such that the cells cannot metabolize and breed and therefore the bacteria are sterilized.

Silver ions or copper ions normally are doped on the surface of the antibacterial housing 110 to a predetermined depth. Along with the use of the electronic device 100, the surface of the antibacterial housing 110 will gradually be worn out. Once the antibacterial housing 110 is over-worn out, silver ions or copper ions will completely disappear and lose the antibacterial effect.

In the present embodiment, the antibacterial housing 110 has a concave hole CV1. The outer opening of the concave hole CV1 gradually changes along with the abrasion of the antibacterial housing 110. Thus, the antibacterial effect can be analyzed according to the size of the outer opening of the concave hole CV1.

Figure 2:
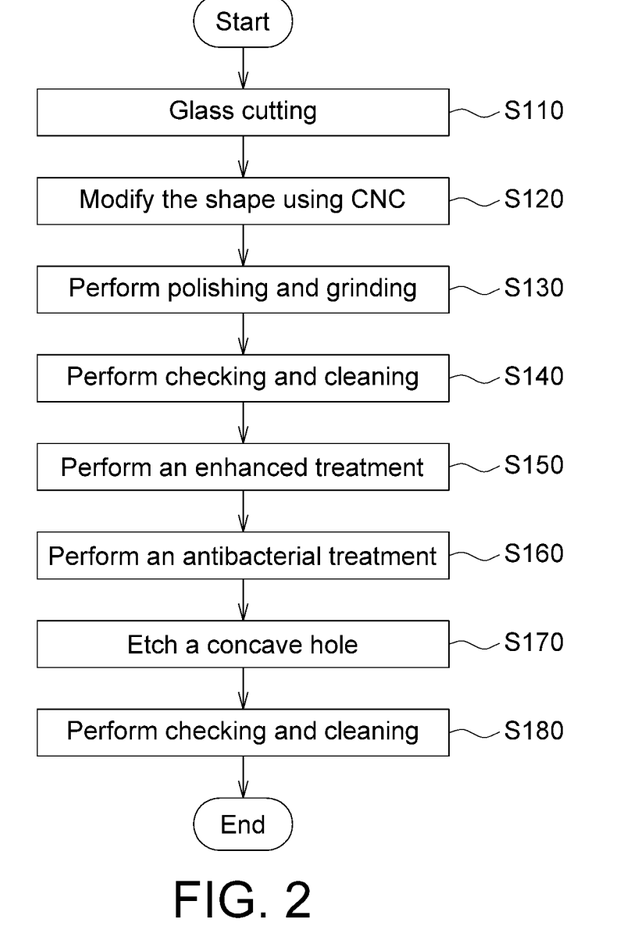
FIG. 2 is a flowchart of a manufacturing process of an antibacterial housing.

Referring to FIG. 2, a flowchart of a manufacturing process of an antibacterial housing 110 is shown. The antibacterial housing 110 is exemplified by a glass panel. In step S110, a glass cutting process is performed. Then, in step S120, a shape modification process is performed using a computer numerical control (CNC) machine. Then, in step S130, a polishing and grinding process is performed. Step 130 can be skipped if no scratches are found. Then, in step S140, a checking and cleaning process is performed. Then, in step S150, an enhanced treatment is performed. The enhanced treatment can be a hot dip treatment. Then, in step S160, an antibacterial treatment is performed. Then, in step S170, a concave hole CV1 is formed using an etching method. In the present step, the concave hole CV1 can be formed using laser etching or chemical etching. Chemical etching includes surface etching and dot etching. The surface etching can be performed through immersing an anti-etching thick/thin film having sparse/dense pattern or through repeated formation and removal of an anti-etching glue into an etching solution, such as cyanofluoric acid. The dot etching is a chemical etching performed by way of inkjet spraying. The dot etching can precisely etch the target position through the control of the size and volume of etching drops. Furthermore, the above etching methods can be combined to increase the yield rate. For example, the laser etching and the dot chemical etching can be combined, or the dot chemical etching and the surface chemical etching can be combined to form the concave hole CV1. Lastly, in step S180, a checking and cleaning process is performed.

Figure 3:
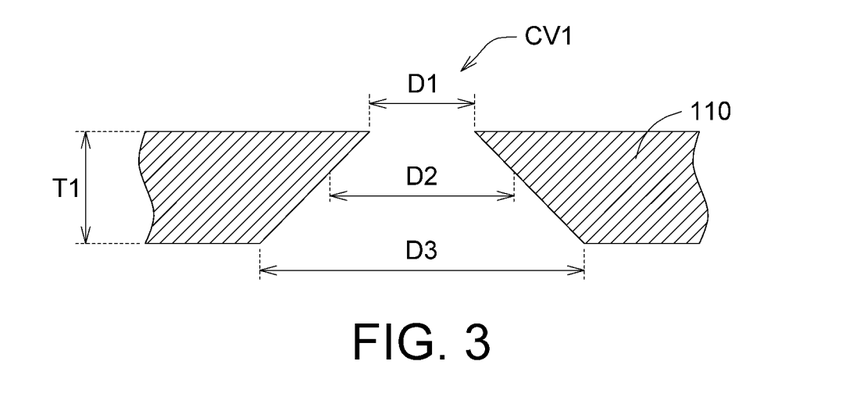
FIG. 3 is a side view of a concave hole.

Referring to FIG. 3, a side view of the concave hole CV1 is shown. As indicated in FIG. 3, the lower portion of the concave hole CV1 is arranged inside the antibacterial housing 110 and the upper portion of the concave hole CV1 I is arranged outside the antibacterial housing 110. The concave hole CV1 gradually shrinks from the inside to the outside. In the example of FIG. 3, the concave hole CV1 passes through the antibacterial housing 110. The outer opening of the concave hole CV1 has a width D1, the middle of the concave hole CV1 has a width D2, and the inner opening of the concave hole CV1 has a width D3. The width D1 is less than the width D2, and the width D2 is less than the width D3. The cross section of the concave hole CV1 is a trapezoid.

Figure 4:
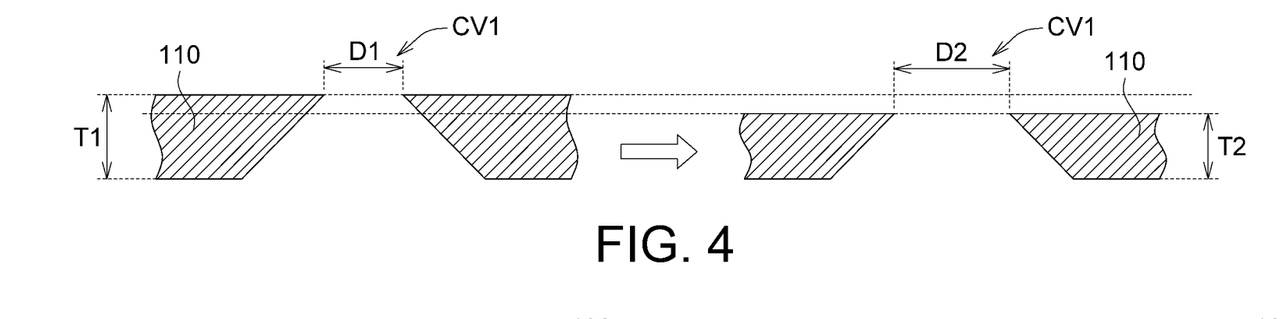
FIG. 4 exemplarily illustrates the wear of an antibacterial housing using a concave hole.

Referring to FIG. 4, the wear of an antibacterial housing 110 is illustrated using a concave hole CV1. As indicated in the left-hand side of FIG. 4, the antibacterial housing 110 has a thickness T1 at the beginning. Meanwhile, the outer opening of the concave hole CV1 has a width D1. As indicated in the right-hand side of FIG. 4, after a period of use, the antibacterial housing 110 has a thickness T2, which is less than the thickness T1. Meanwhile, the outer opening of the concave hole CV1 has a width D2. Since the concave hole CV1 gradually shrinks from the inside to the outside, the antibacterial effect can be analyzed according to the width of the outer opening. The smaller the outer opening, the better the antibacterial effect.

Figure 5:
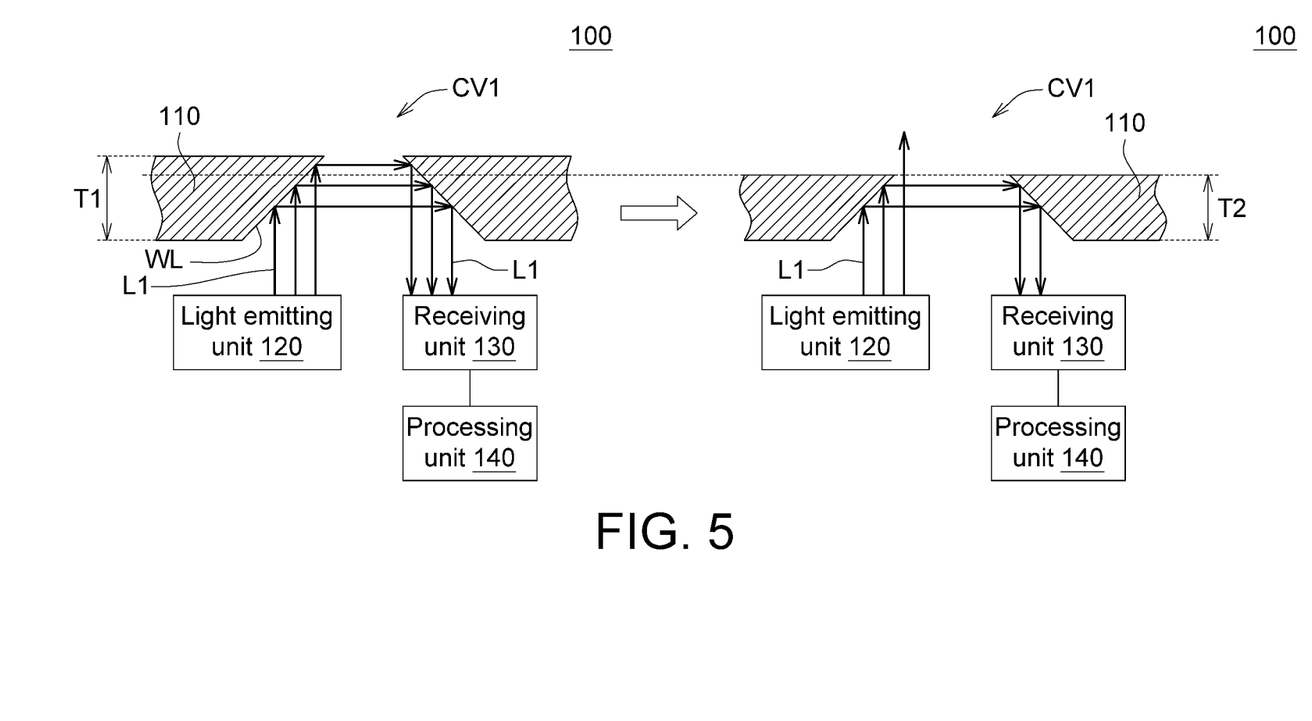
FIG. 5 is a schematic diagram of an electronic device automatically analyzing the antibacterial effect.

Referring to FIG. 5, a schematic diagram of an electronic device 100 automatically analyzing the antibacterial effect is shown. The electronic device 100 includes an antibacterial housing 110, a light emitting unit 120, a light receiving unit 130 and a processing unit 140. The light emitting unit 120 is arranged under the concave hole CV1 of the antibacterial housing 110. The light emitting unit 120 is used for emitting a detection light L1 toward the concave hole CV1. The light emitting unit 120 can be an LED, a laser light source or a light bulb. The light emitting unit 120 emits a detection light L1 towards the inclined side wall WL of the concave hole CV1. The detection light L1 is reflected by the inclined side wall WL to enter the light receiving unit 130. The light receiving unit 130 can be a light sensor or a photoresistor. The light receiving unit 130 receives the detection light L1 reflected from the inclined side wall WL of the concave hole CV1. The processing unit 140 can be a processor, a circuit, a chip, a circuit board or a storage device storing programming codes.

As indicated in the left-hand side of FIG. 5, the antibacterial housing 110 has the thickness T1 at the beginning, and most of the detection light L1 can be reflected to the light receiving unit 130. As indicated in the right-hand side of FIG. 5, when the antibacterial housing 110 is worn out to the thickness T2, only a small portion of the detection light L1 can be reflected to the light receiving unit 130.

The processing unit 140 analyzes the degree of abrasion of the antibacterial housing 110 according to an amount of light of the detection light L1 to detect the antibacterial effect. That is, the processing unit 140 does not actually measure the thickness of the antibacterial housing 110. Instead, based on the design that the concave hole CV1 gradually shrinks from the inside to the outside, the processing unit 140 estimates the thickness of the antibacterial housing 110 according to an amount of light of the detection light L1 which varies with the thickness of the antibacterial housing 110.

In above embodiments, the light receiving unit 130 and the processing unit 140 are arranged inside the electronic device 100. In other embodiments, the light receiving unit and the processing unit can be arranged inside another portable device. Detailed descriptions of the embodiments are disclosed below.

Figure 6:
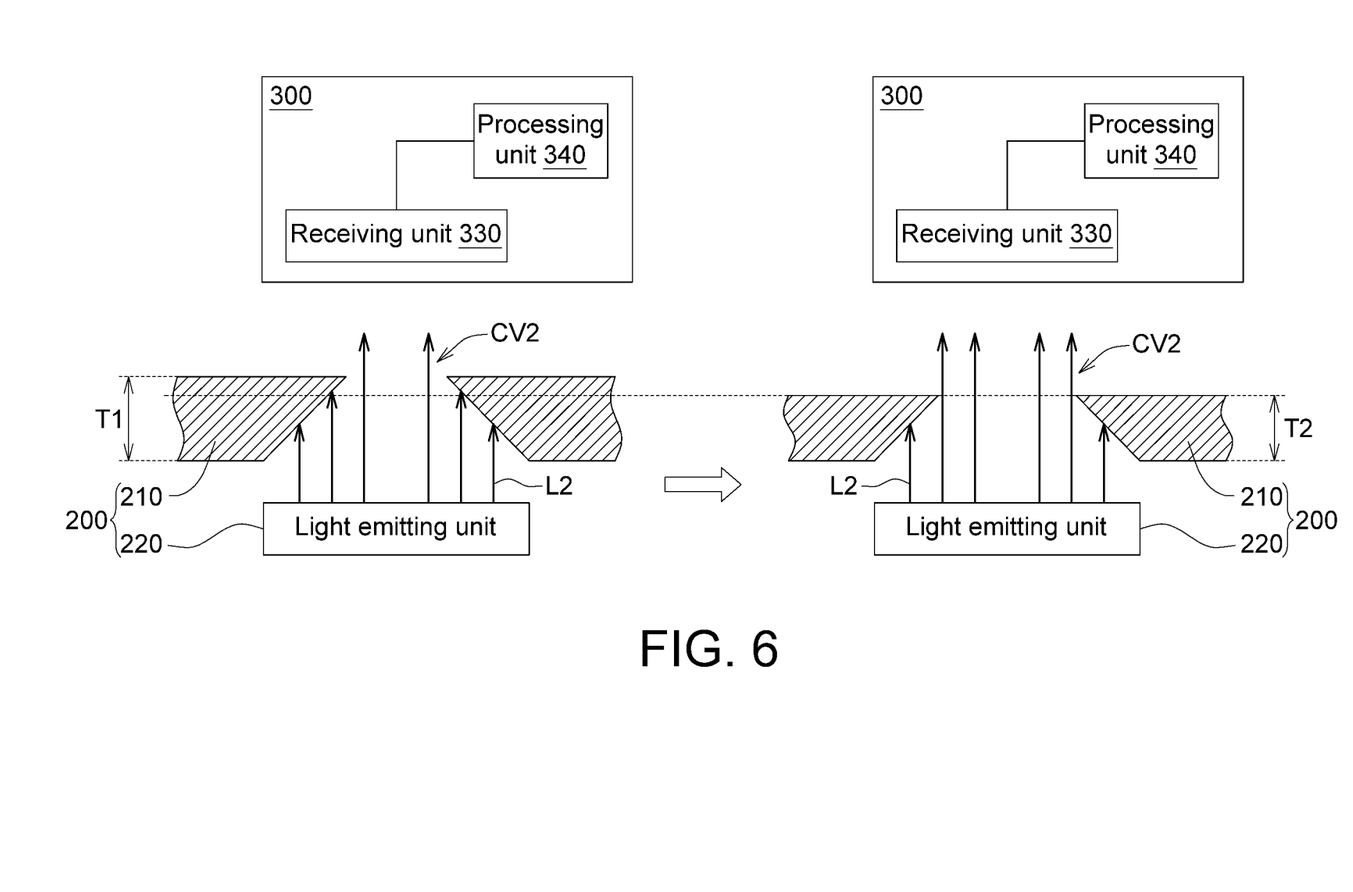
FIG. 6 is a schematic diagram of an electronic device and a portable device according to another embodiment.

Referring to FIG. 6, a schematic diagram of an electronic device 200 and a portable device 300 according to another embodiment is shown. The electronic device 200 includes an antibacterial housing 210 and a light emitting unit 220. The portable device 300 includes a light receiving unit 330 and a processing unit 340. The antibacterial housing 210 has a concave hole CV2. The concave hole CV2 gradually shrinks from the inside to the outside. The light emitting unit 220 is arranged under the concave hole CV2 of the antibacterial housing 210. The light emitting unit 220 emits a detection light L2 towards the concave hole CV2. The portable device 300 receives the detection light L2 reflected from the concave hole CV2 and analyzes an antibacterial effect of the antibacterial housing 210 according to the detection light L2.

As indicated in the left-hand side of FIG. 6, the antibacterial housing 210 has the thickness T1 at the beginning, and only a small portion of the detection light L2 can pass through the outer opening of the concave hole CV2 and reach the light receiving unit 330. As indicated in the right-hand side of FIG. 6, when the antibacterial housing 210 is worn out to the thickness T2, a larger portion of the detection light L2 can pass through the outer opening of the concave hole CV2 and reach the light receiving unit 330.

The processing unit 340 analyzes the degree of abrasion of the antibacterial housing 210 according to an amount of light of the detection light L2 to detect the antibacterial effect. That is, the processing unit 340 does not actually measure the thickness of the antibacterial housing 210. Instead, based on the design that the concave hole CV2 gradually shrinks from the inside to the outside, the processing unit 140 estimates the thickness of the antibacterial housing 110 according to an amount of light of the detection light L2 which varies with the thickness of the antibacterial housing 110.

Figure 7:
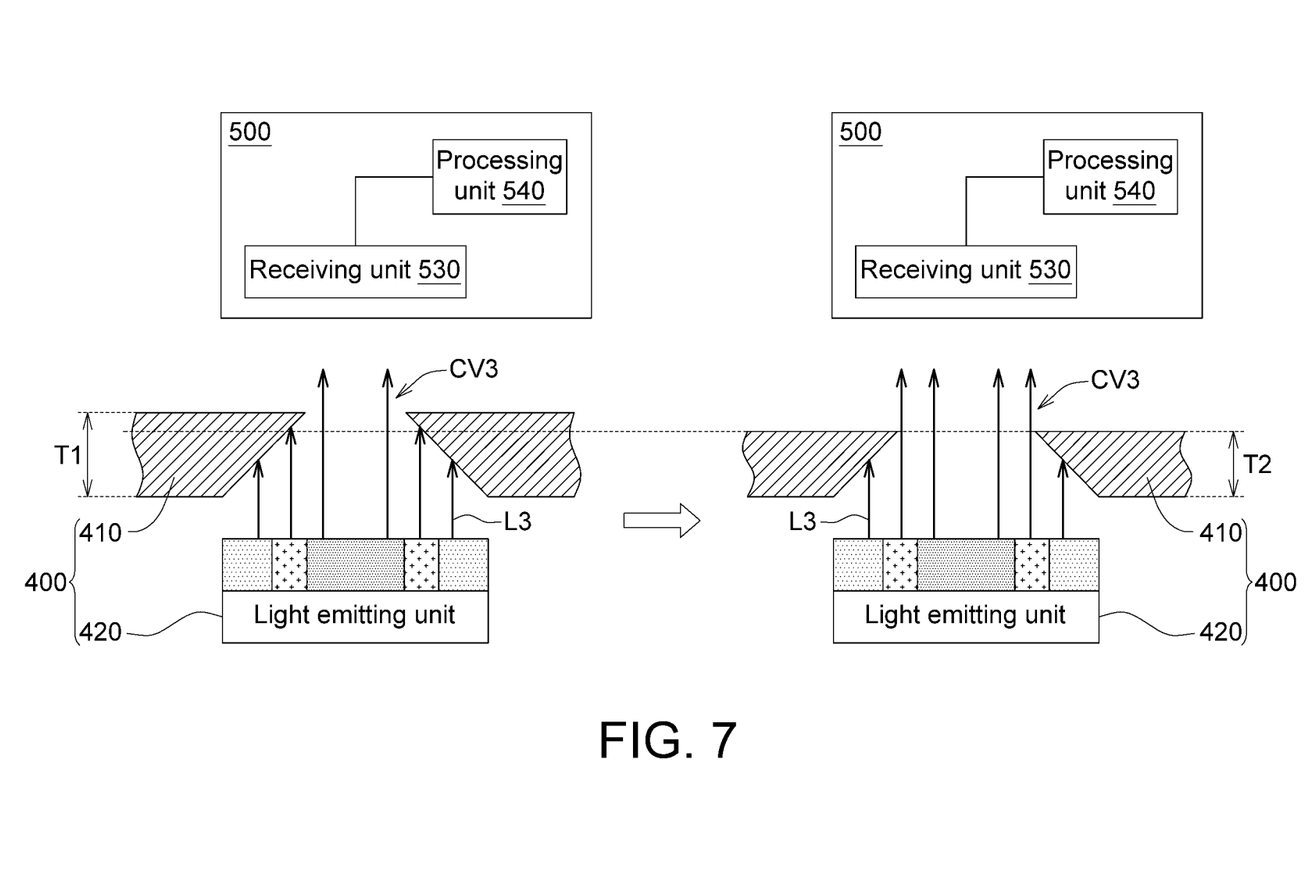
FIG. 7 is a schematic diagram of an electronic device and a portable device according to another embodiment.

Referring to FIG. 7, a schematic diagram of an electronic device 400 and a portable device 500 according to another embodiment is shown. The electronic device 400 includes an antibacterial housing 410 and a light emitting unit 420. The portable device 500 includes a light receiving unit 530 and a processing unit 540. The antibacterial housing 410 has a concave hole CV3. The concave hole CV3 gradually shrinks from the inside to the outside. The light emitting unit 420 is arranged under the concave hole CV3 of the antibacterial housing 410. The light emitting unit 420 emits a detection light L3 towards the concave hole CV3. The color of the detection light L3 varies from the center to the outside. The portable device 500 receives the detection light L3 reflected from the concave hole CV3 and analyzes an antibacterial effect of the antibacterial housing 410 according to the detection light L3.

As indicated in the left-hand side of FIG. 7, the antibacterial housing 410 has the thickness T1 at the beginning, and only the central portion of the detection light L3 can pass through the outer opening of the concave hole CV3 and reach the light receiving unit 530. As indicated in the right-hand side of FIG. 7, when the antibacterial housing 410 is worn out to the thickness T2, the outer portion of the detection light L3 also can pass through the outer opening of the concave hole CV3 and reach the light receiving unit 530.

The processing unit 540 analyzes the degree of abrasion of the antibacterial housing 210 according to the color of the detection light L3 to detect the antibacterial effect. That is, the processing unit 540 does not actually measure the thickness of the antibacterial housing 410. Instead, based on the design that the concave hole CV3 gradually shrinks from the inside to the outside, the processing unit 540 estimates the thickness of the antibacterial housing 410 according to the color of the detection light L3 which varies with the thickness of the antibacterial housing 410.

Figure 8:
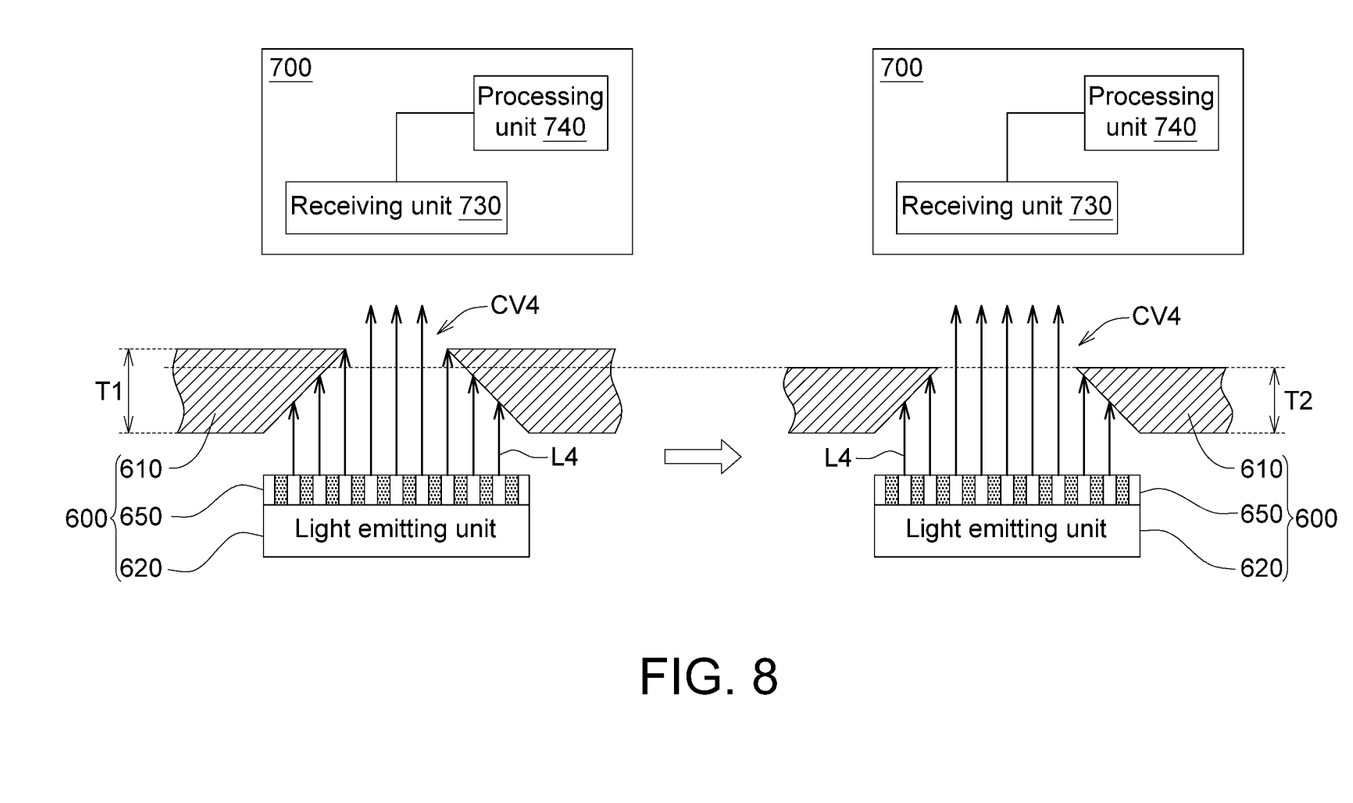
FIG. 8 is a schematic diagram of an electronic device and a portable device according to another embodiment.

Referring to FIG. 8, a schematic diagram of an electronic device 600 and a portable device 700 according to another embodiment is shown. The electronic device 600 includes an antibacterial housing 610, a light emitting unit 620 and a light grid 650. The portable device 700 includes a light receiving unit 730 and a processing unit 740. The antibacterial housing 610 has a concave hole CV4. The concave hole CV4 gradually shrinks from the inside to the outside. The light emitting unit 620 is arranged under the concave hole CV4 of the antibacterial housing 610. The light emitting unit 620 emits a detection light L4 towards the concave hole CV4. The light grid 650 is arranged between the light emitting unit 620 and the concave hole CV4, such that the detection light L4 shows several light patterns. The portable device 700 receives the detection light L4 reflected from the concave hole CV4 and analyzes an antibacterial effect of the antibacterial housing 610 according to the detection light L4.

As indicated in the left-hand side of FIG. 8, the antibacterial housing 610 has the thickness T1 at the beginning, and only the central portion of the detection light L4 can pass through the outer opening of the concave hole CV4 and reach the light receiving unit 730. As indicated in the right-hand side of FIG. 8, when the antibacterial housing 610 is worn out to the thickness T2, the outer portion of the detection light L4 also can pass through the outer opening of the concave hole CV4 and reach the light receiving unit 730.

The processing unit 740 can analyze the degree of abrasion of the antibacterial housing 610 according to a number of light patterns of the detection light L4 to detect the antibacterial effect. That is, the processing unit 740 does not actually measure the thickness of the antibacterial housing 610. Instead, based on the design that the concave hole CV4 gradually shrinks from the inside to the outside, the processing unit 740 estimates the thickness of the antibacterial housing 610 according to a number of light patterns of the detection light L4 which varies with the thickness of the antibacterial housing 610.

Figure 9:
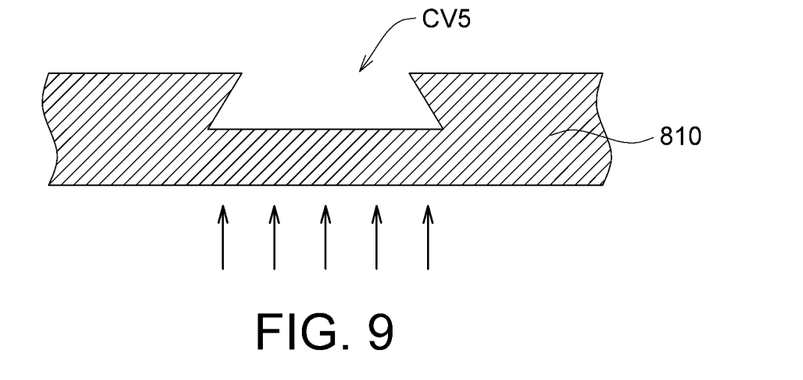
FIG. 9 is a schematic diagram of a concave hole according to another embodiment.

Apart from above embodiments, the concave hole can be designed as follows. Referring to FIG. 9, a schematic diagram of a concave hole CV5 according to another embodiment is shown. As indicated in FIG. 9, the concave hole CV5 does not pass through the antibacterial housing 810 and only the outer opening of the concave hole CV5 faces the outside of the antibacterial housing 810.

Figure 10:
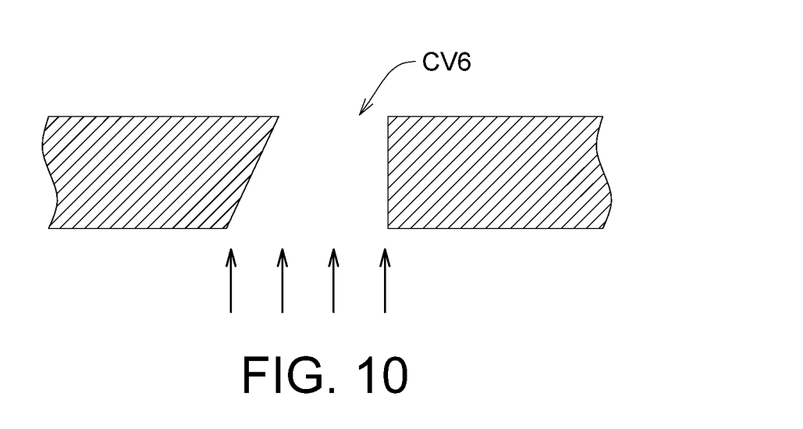
FIGS. 10 to 11 are schematic diagrams of concave holes according to other embodiments.
Figure 11:
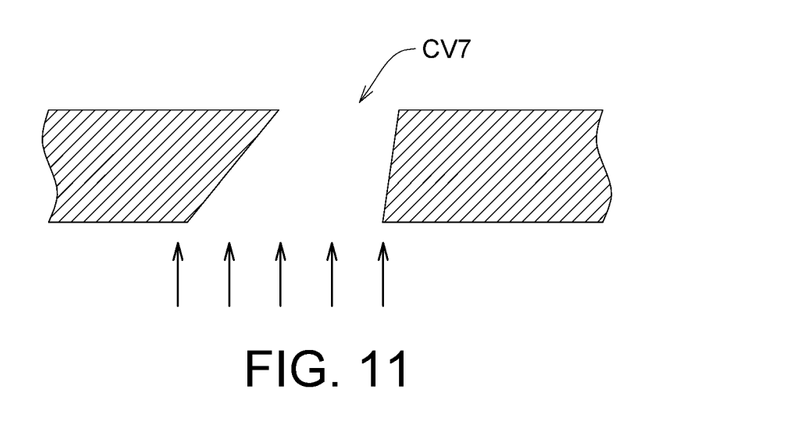

Referring to FIGS. 10 to 11, schematic diagrams of a concave hole CV6 and a concave hole CV7 according to other embodiments are shown. As indicated in FIGS. 10 to 11, the concave holes CV6 and CV7 form an asymmetric structure, but the concave hole CV6 still gradually shrinks from the inside to the outside.

Figure 12:
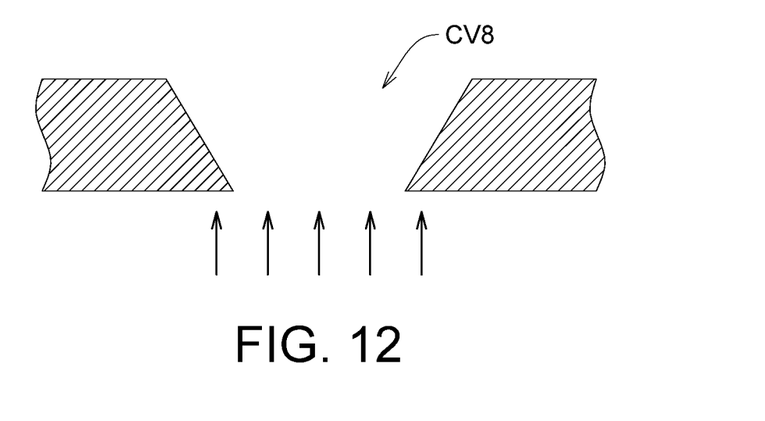
FIGS. 12 to 13 are schematic diagrams of concave holes according to other embodiments.
Figure 13:
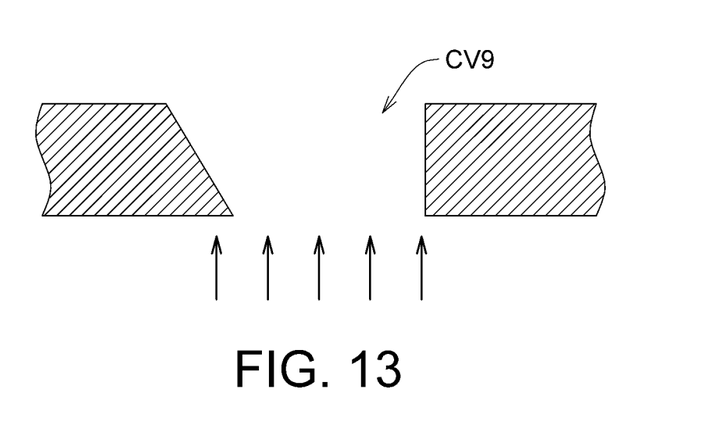

Referring to FIGS. 12 to 13, schematic diagrams of a concave hole CV8 and a concave hole CV9 are shown. As indicated in FIGS. 12 to 13, the concave holes CV8 and CV9 gradually expand from the inside to the outside. Along with the change in the thickness of the antibacterial housing, the sizes of the concave holes CV8 and CV9 also change, and the thickness of the antibacterial housing can be estimated according to the change in the light.

Besides, the cross sections of the concave holes CV1 to CV9 can be round, oval, squared or triangular.

As disclosed in above embodiments, based on the design that the concave hole gradually shrinks from the inside to the outside, the detection light can generate different changes along with the change in the thickness of the antibacterial housing, and the antibacterial effect of the antibacterial housing can be estimated according to the thickness of the antibacterial housing.

While the invention has been described by way of example and in terms of the preferred embodiment(s), it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An electronic device with antibacterial effect detection, comprising:
   an antibacterial housing having a concave hole, which gradually shrinks from an inside of the antibacterial housing to an outside of the antibacterial housing;
   a light emitting unit arranged under the concave hole of the antibacterial housing, wherein the light emitting unit is used for emitting a detection light toward an inclined side wall of the concave hole;
   a light receiving unit arranged under the concave hole of the antibacterial housing, wherein the light receiving unit is used for receiving the detection light reflected from the inclined side wall of the concave hole; and a processing unit used for analyzing an antibacterial effect of the antibacterial housing according to the detection light.

2. The electronic device according to claim 1, wherein the concave hole passes through the antibacterial housing.

3. The electronic device according to claim 1, the concave hole has only one outer opening, which faces the outside of the antibacterial housing.

4. The electronic device according to claim 1, wherein a cross section of the concave hole is a circle, an ellipse, a square or a triangle.

5. The electronic device according to claim 1, wherein the processing unit analyzes a degree of abrasion of the antibacterial housing according to an amount of light of the detection light.

6. The electronic device according to claim 1, wherein the concave hole forms an asymmetric structure.

7. The electronic device according to claim 1, wherein the concave hole does not pass through the antibacterial housing.

8. An electronic device with antibacterial effect detection, comprising:
    an antibacterial housing having a concave hole, which gradually shrinks from an inside of the antibacterial housing to an outside of the antibacterial housing; and
    a light emitting unit arranged under the concave hole of the antibacterial housing, wherein the light emitting unit is used for emitting a detection light toward the concave hole, and a portable device receives the detection light reflected from the concave hole and analyzes an antibacterial effect of the antibacterial housing according to the detection light.

9. The electronic device according to claim 8, wherein a color of the detection light varies from a center of the concave hole to an outside of the concave hole.

10. The electronic device according to claim 8, further comprising:
    a light grid arranged between the light emitting unit and the concave hole, such that the detection light shows a plurality of light patterns.

11. The electronic device according to claim 8, wherein the concave hole passes through the antibacterial housing.

12. The electronic device according to claim 8, the concave hole has only one outer opening, which faces the outside of the antibacterial housing.

13. The electronic device according to claim 8, wherein a cross section of the concave hole is a circle, an ellipse, a square or a triangle.

14. The electronic device according to claim 8, wherein the concave hole forms an asymmetric structure.

15. The electronic device according to claim 8, wherein the concave hole does not pass through the antibacterial housing.

16. A portable device, comprising:
    a light receiving unit used for receiving a detection light reflected from an inclined side wall of a concave hole of an antibacterial housing of an electronic device, wherein the concave hole gradually shrinks from an inside of the antibacterial housing to an outside of the antibacterial housing; and
    a processing unit used for analyzing an antibacterial effect of the antibacterial housing according to the detection light.

17. The portable device according to claim 16, wherein the processing unit analyzes a degree of abrasion of the antibacterial housing according to an amount of light of the detection light.

18. The portable device according to claim 16, wherein the processing device analyzes a degree of abrasion of the antibacterial housing according to a color of the detection light.

19. The portable device according to claim 16, wherein the processing device analyzes a degree of abrasion of the antibacterial housing according to a number of light patterns of the detection light.

20. The portable device according to claim 16, wherein the concave hole forms an asymmetric structure.

* * * * *